United States Patent
Mandava et al.

(10) Patent No.: US 10,440,954 B2
(45) Date of Patent: Oct. 15, 2019

(54) INCREASED ALMOND YIELDS WITH BRASSINOSTEROID APPLICATION

(71) Applicant: Repar Corporation, Silver Spring, MD (US)

(72) Inventors: Naga Bhushan Mandava, Potomac, MD (US); Carlos Sotomayor, Santiago (CL)

(*) Notice: Subject to any disclaimer, the term of this patent is extended or adjusted under 35 U.S.C. 154(b) by 0 days.

(21) Appl. No.: 15/852,751

(22) Filed: Dec. 22, 2017

(65) Prior Publication Data

US 2018/0332852 A1 Nov. 22, 2018

Related U.S. Application Data

(60) Provisional application No. 62/509,362, filed on May 22, 2017.

(51) Int. Cl.
*A01N 45/00* (2006.01)
*A01N 47/36* (2006.01)
*A01N 43/22* (2006.01)

(52) U.S. Cl.
CPC ............ *A01N 45/00* (2013.01); *A01N 43/22* (2013.01); *A01N 47/36* (2013.01); *A01N 2300/00* (2013.01)

(58) Field of Classification Search
None
See application file for complete search history.

(56) References Cited

U.S. PATENT DOCUMENTS 3,250,675 A * 5/1966 Frohberger ............ C07C 39/15
514/736
5,880,110 A 3/1999 Kasukabe

FOREIGN PATENT DOCUMENTS

WO WO-2010146046 A1 * 12/2010 ............ A01G 31/00

OTHER PUBLICATIONS

Maita et al( The effect of three plant bioregulators on pollen germination, pollen tube growth and fruit set in almond [Prunus dulcis (Mill.) D.A. Webb] cvs. Non Pareil and Carmel, Electronic Journal of Biotechnology (2015), vol. 18, pp. 381-386) (Year: 2015).*

* cited by examiner

*Primary Examiner* — Alton N Pryor
(74) *Attorney, Agent, or Firm* — Steve O'Donnell

(57) ABSTRACT

Methods for increasing the yield of almond trees by the application of certain plant growth regulators are disclosed. In one embodiment, a brassinosteroid is applied to a variety of the species *Prunus dulcis* in the growth stage two weeks after full bloom. In another embodiment, the almond trees are treated at the time of petal fall with a brassinosteroid during the formation the ovaries and nutlets. Non-brassinosteroid plant growth regulators such as Forchlorfenuron and Gibberellic acid may be applied with a brassinosteroid to further promote growth.

The inventors hypothesize that changes in reproductive physiology such as increasing pollen tube growth and pollen germination rates that ultimately result in greater crop yield are promoted by applications of brassinosteroids.

8 Claims, 7 Drawing Sheets

Brassinolide

Epi-brassinolide

HomoBrassinolide

Gibberellic Acid

Forchlorfenuron

Castasterone

Homocastasterone

Figure 8

TABLE 1. Results of HBR and CPPU Treatments

| TREATMENT | WHOLE NUT (g) | KERNAL (g) |
|---|---|---|
| CONTROL | 2.51 | 0.99 |
| HBR (1 PPM) | 2.83 | 1.03 |
| HBR (10 PPM) | 2.87 | 0.96 |
| HBR (1 PPM) + CPPU (10 PPM) | 3.01 | 1.08 |
| HBR (10 PPM) + CPPU (10 PPM) | 2.83 | 1.04 |
| HBR (10 PPM) + CPPU (1 PPM) | 2.73 | 1.05 |

Figure 9

TABLE 2. Results of HBR and CPPU Treatments

| TREATMENT | % FRUIT SET | SEED DRY WEIGHT (g) |
|---|---|---|
| CONTROL | 42.01 | 0.9 |
| HBR (1 PPM) | 47.59 | 1.02 |
| HBR (10 PPM) | 43.06 | 0.99 |
| HBR (10 PPM) + CPPU (10 PPM) | 42.29 | 1.05 |

Figure 10

TABLE 3. Results of BRs and GA3 Treatments.

| TREATMENT | POLLEN GERMINATION FOUR HOURS POST TREATMENT | POLLEN TUBE GROWTH 24 HOURS POST TREATMENT | FRUIT SET AT 50 DAYS POST TREATMENT |
|---|---|---|---|
| GA3 | 58.4 | 589.5 | 36.7 |
| BR | 58 | 682.2 | 46.1 |
| CONTROL | 49.9 | 586.7 | 38.6 |

INCREASED ALMOND YIELDS WITH BRASSINOSTEROID APPLICATION

FIELD OF THE INVENTION

The subject matter of this application pertains to a method for using Plant Growth Regulators (PGRs) to produce almond nuts with improved characteristics such as: increased whole nut size, kernel size, shell size and hull size, as well as increased fruit set. More precisely, the subject matter of this application pertains to methods for increasing almond nut size, kernel size, shell size and hull size, as well as increased fruit set with the use of at least one brassinosteroid selected from the group comprising brassinolide (CAS #74174-44-0), and epibrassinolide (CAS #78821-42-8), homobrassinolide (CAS #80483-89-2), or at least one brassinosteroid precursor from the group comprising Castasterone (CAS #80736-41-0), and 28-Homocastasterone (CAS #83509-42-6). Non-brassinosteroid plant growth regulators such as gibberellic acid (CAS #77-06-5) and Forchlorfenuron (CAS #68157-60-8) may be used with the selected brassinosteroid to enhance growth.

BACKGROUND

Commonly the word "almond" refers to the edible seed of the almond tree (*Prunus dulcis*). There are several types of almonds including nonpareil, Carmel, California, and Mission Type, produced by varieties of almond trees.

Although almonds are grown across the world, most are produced in the United States. According to the February 2017 USDA report, "Tree Nuts: World Markets and Trade," global almond production is 1.2 million metric tons of shelled product, of which over 920,000 tons are produced in the United States (https://apps.fas.usda.gov/psdonline/circulars/TreeNuts.pdf).

Profitability of the almond crop is subject to demand and the costs of production. Demand has increased in recent years, and now the yearly production is roughly 130,000 tons more than it was just four years ago. Modern conventional cultivation methods are useful to maximize yield but the economics of almond production is still dependent on the trees' genetics.

Almond tree flowers, as well as other flowers, are comprised of several reproductive parts. The reproductive process of almond trees can be described as when the stamen produces pollen which then germinates once it comes into contact with the stigma. In response to germination, a pollen tube develops extending down from the stigma to the flower's ovule. Pollen moves through the pollen tube to the ovule and the resulting contact between pollen and ovule is fertilization, allowing both seeds and fruits to develop. The effective pollination period (EPP) is the time frame during which pollination can produce fruit most effectively and is determined by the longevity of the ovule and the time needed for the pollen tube to grow from the stigma to the ovule after germination. Although some plants self-fertilize, others such as almond trees require cross-pollination. For almond trees the most effective window for fertilization is within the first two days of a flower opening, and after 3-4 days, the flower cannot be fertilized. Studies have shown that it takes 96 to 120 hours for pollen tubes to grow through the flower to reach the embryo sac (Griggs, W. H.; Iwakiri, B. Pollen tubes growth in almond flowers. California Agriculture, 1975 29(7):4-7) so presumably the sooner pollination occurs after a flower opens, the greater the chance of successful fertilization and fruit set. By this virtue, actions or treatments that increase pollen tube growth rate should expand the effective pollination period (EPP), resulting in increased fertilization and ultimately, an increase in the fruit set.

Brassinosteroids ("BRs") and gibberellins ("GAs") are two families of plant growth regulating hormones.

Brassinosteroids are found throughout the plant kingdom and have unique growth promoting activity when applied to plants (Mandava, N. B. *Plant growth promoting brassinosteroids*. Annual Review of Plant Physiology and Plant Molecular Biology 1988, 39; 23-52). Brassinolide, the first identified brassinosteroid, was first isolated in 1979 from rape (*Brassica napus* L.) pollen, where it is present in quantities up to 200 parts per billion.

Since the discovery of the chemical structure of brassinolide ("BL" CAS #74174-44-0, FIG. 1), it has been synthesized and analogues have been developed, often from readily available plant sterols. Among the brassinosteroids shown to have similar biological activity as BL are epibrassinolide ("epi BL" CAS #78821-42-8, FIG. 2), homobrassinolide ("HBR" CAS #80483-89-2, FIG. 3), castasterone ("CS" CAS #80736-41-0, FIG. 6), 28-homocastasterone ("HCS" CAS #83509-42-6, FIG. 7). Castasterone and 28-homocastasterone are converted to BL and HBR, respectively, in vivo.

BRs are reported to increase yields and improve stress resistance of several crop plants (Cutler, H. G., et. al. *Brassinosteroids: chemistry bioactivity, and applications*. ACS symposium Series 474. Washington D.C., 1991; American Chemical Society). Treatments with BRs are effective ways of increasing yield of many crops even in cases of drought, extreme temperatures, and improper soil salinity. For example, in almond trees, BRs have been shown to counteract the slowed pollen tube growth rate caused by lower temperatures (Bernard, D. and Socias, R. I Company. *Characterization of Some Self-compatible Almonds. II. Flower Phenology and Morphology*. HortScience, 1995, 30(2): 321-324).

Gibberellins were first isolated in 1935 and are known in the art for their involvement in seed germination. Gibberellins are also important modulators of plant gene expression and can stimulate stem and root growth. Gibberellic acid ("GA$_3$," CAS #77-06-5, FIG. 4) promotes growth and elongation of cells and stimulates plant growth when used in small amounts.

Forchlorfenuron ("CPPU," FIG. 5) is another plant growth regulator which can improve fruit size and fruit set of blueberries, grapes, and kiwi. https://www.epa.gov/site/production/file/2015-04/documents/exhibit_e.pdf Methods of increasing almond fertilization and increasing almond kernel size can result in a higher return on investment for growers.

SUMMARY

The subject matter of this application provides a method for increasing almond tree fruit set and almond kernel size by applying plant growth regulators during critical periods of an almond tree's fertilization period.

More specifically the subject matter of this application pertains to methods of increasing almond yield by the application of one or more members of the group consisting of brassinosteroids, gibberellins, and forchlorfenuron, at certain developmental points in the tree's reproductive cycle.

The inventors hypothesize that treatment of almond flowers with a brassinosteroid, with or without other plant growth regulators, increases fruit set by promoting pollen tube growth, increasing the number of pollen tubes which reach the ovule, and increasing pollen tube loading. In vitro data (not shown) indicates a repeated trend of increased pollen tube growth and germination rates although the exact mechanism through which treatment increases fruit set has yet to be determined.

BRIEF DESCRIPTION OF THE FIGURES

FIG. 8 is a summary table of results of Experiment 1.
FIG. 9 is a summary table of results of Experiment 2.
FIG. 10 is a summary table of results of Experiment 3.

DETAILED DESCRIPTION OF THE SUBJECT MATTER

Figure 1:
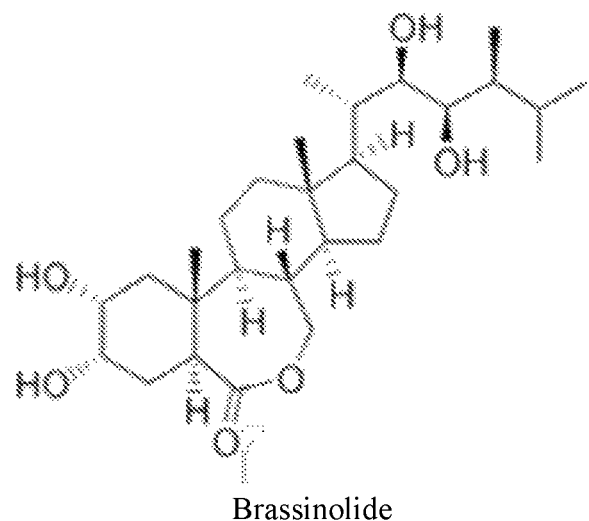
FIG. 1 is the chemical structure of brassinolide.

The following description and referenced figures illustrate embodiments of the subject matter of this application. They are not intended to limit the scope of the claims. Those familiar with the art may recognize that other embodiments of the disclosed method are possible. For example, analogues of the chemicals used having the same or substantially similar growth-promoting properties should be considered equivalent to the claimed chemical. All such alternative embodiments should be considered within the scope of the application's claims.

The fruit of the almond tree (the "nut" or "whole nut") contains three parts, the hull, the shell, and the kernel. The hull is the outermost structure of the nut that can be green or brown colored, and is what one would see if looking at the untouched nut hanging from on a tree. Within the hull is the shell, which is a hard covering surrounding the edible kernel. In common parlance, "almond" is usually used to refer to the edible kernal of the almond tree (*Prunus dulcis*). There are several other types of almonds including nonpareil, Carmel, California, and Mission Type, produced by varieties of almond trees. Unless specified, the term "almond" refers to the kernals from all almond trees. Collectively, the brassinosteroids, gibberellins, and forchlorfenuron may be referred to as "plant growth regulators" or "PGRs." Almond yield is the number of almonds produced by an almond tree or group of trees. An almond tree's blossoms go though several stages. The pink bud stage, the popcorn bud stage, full bloom, and petal fall are of particular interest to the subject matter of this application. The pink bud stage occurs in early blossom development when the first pink tipped buds emerge and start to open. Popcorn bud stage follows, and is marked by the appearance of several white flowers. Full bloom is next, and is characterized by fully opened flowers with larger petals and longer stamen surrounding the pistil than in the popcorn bud stage. Full bloom is also when fertilization can take place. Following full bloom is petal fall stage, in which the flowers petals droop and eventually fall off. At this point fertilized pistils will normally begin to produce fruit, initially forming what are known as nutlets, or small nuts. Not all fertilized pistils will produce fruit however, so the term "fruit set" is used to refer to successful fruiting. Since not all flowers on all trees will develop at the same exact time, discussions of when to apply any treatment to a population of trees must take into account this variability. For example, although an individual flower is capable of being fertilized during its full bloom stage, in a population of trees some flowers will be in full bloom stage, while some are likely in in popcorn bud stage and still others in petal fall stage. Accordingly, a user must approximate when a majority of flowers are at the proper stage for treatment. The methods for increasing fertilization, fruit set, and kernel size of almonds disclosed in this specification are based on experimental findings that application of PGRs during critical development periods can induce morphological changes to the nut and the reproductive physiology of the flower and increase almond yield.

Homobrassinolide, forchlorfenuron, and gibberellic acid are commercially available and may be diluted as needed prior to application. For example, the HBR used was made by diluting a 0.1% stock solution of HBR, EPA Reg No. 69361-49 from Repar Corporation, Silver Spring, Md. as needed. HBR is not stable at alkaline pH levels so the pH level should be adjusted after dilution to no greater than 7.0, and optimally between 4.0 and 5.0.

It should be understood that the concentrations discussed are not necessarily exact. Typically a user would purchase a stock solution of a plant growth regulator and dilute it one or more times to reach their target concentration. Each measurement can have some amount of error such as that due to the accuracy of the measuring means or that due to the measurer's level of care. Accordingly, each concentration stated should be understood to be an approximation of the actual concentration.

The findings which comprise the subject matter of this application are outlined by the following three experiments.

EXPERIMENT 1.

Almond trees in a Fresno, Calif. orchard were treated with PGRs to assess treatment effects on nut and kernel mass at harvest.

Fifteen trees each received three experimental treatments on single branches. Each experimental treatment was applied to four different branches. The treatments were determined using a randomized complete block design. Flowers on each experimental branch were counted at pink bud to popcorn bloom stage to determine a pre-treatment baseline.

Half of the branches were sprayed with the treatment solution when the nutlet length was approximately 3-6 mm (Time A), corresponding to approximately 80% petal fall. The other half of the branches were sprayed when nutlet length was approximately 6-15 mm (Time B).

Figure 3:
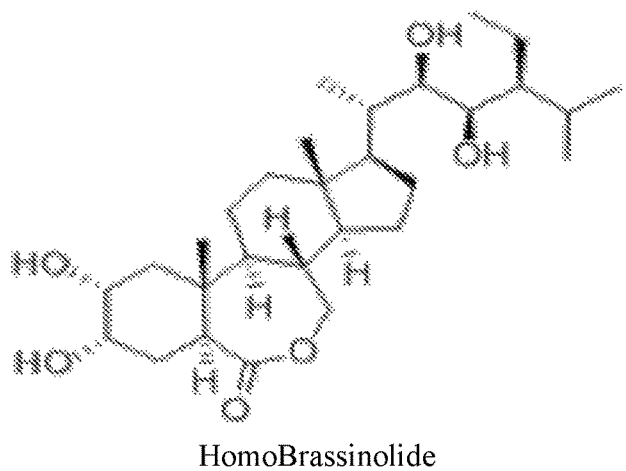
FIG. 3 is the chemical structure of homobrassinolide.
Figure 5:
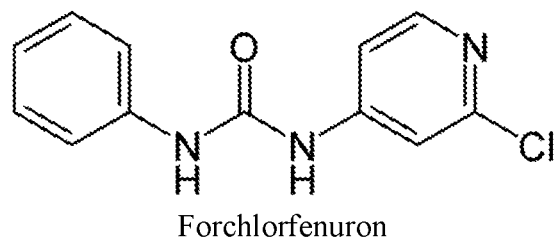
FIG. 5 is the chemical structure of forchlorfenuron.
Figure 6:
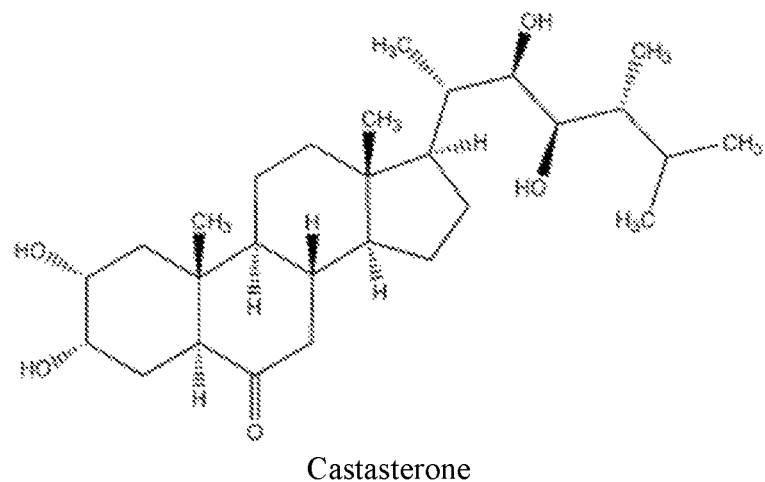
FIG. 6 is the chemical structure of castasterone.
Figure 7:
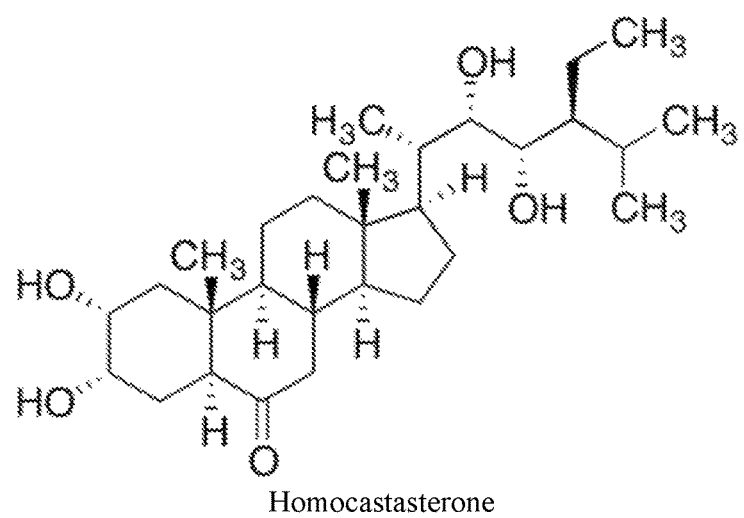
FIG. 7 is the chemical structure of homocasterone.
Figure 11:
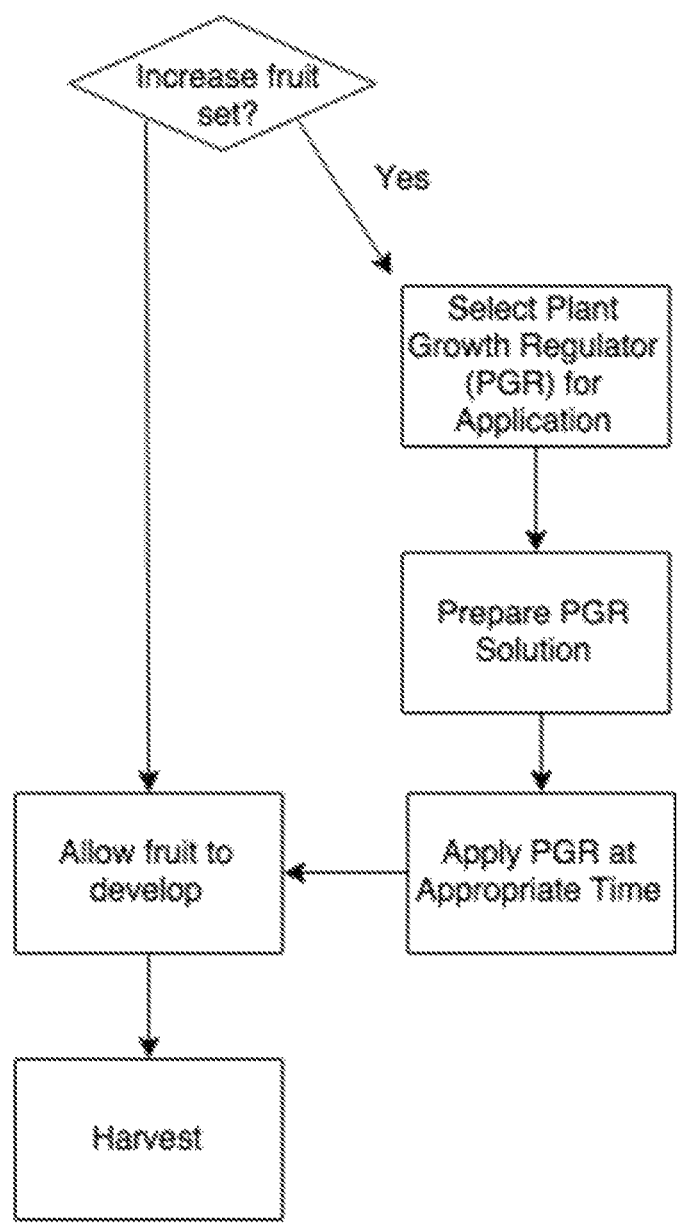
FIG. 11 is a flow chart of the disclosed method.

One control and ten treatments were assessed: a control containing no PGRs; a solution containing HBR (FIG. 3) at a rate of 1 part per million (ppm); a 10 ppm solution of HBR; a 1 ppm HBR solution further comprising 10 ppm of CPPU (FIG. 5); a solution of 10 ppm HBR and 10 ppm CPPU; and a solution of 10 ppm HBR and 1 ppm CPPU. Each treatment was applied at Time A and B with hand spraying pumps until the branch was wet and excess solution ran off the branch.

Treated branches were periodically observed for phytotoxicity and samples were taken at 146 days after the first treatments (corresponding to 144 days after the second treatment). At harvest, the nuts were dried, weighed out on a scale, and then separated into hulls, shells, and kernels. The weight of the kernels and hulls were measured, and shell weight was determined by subtracting the combined weight of the hull and kernel from the total weight of the nut, as the shells had to be destroyed in the separation process.

In terms of kernel weight, there was no significant difference between application Times A and B. The masses of the whole nuts and kernels receiving each treatment were determined and average masses are shown in Table 1 (FIG. 8). As compared to the control, treatment with a solution of 1 ppm HBR with 10 ppm CPPU resulted in the largest increase in whole nut and kernel mass.

EXPERIMENT 2.

The effects of HBR on nut size and fruit set were studied in a population of 20 year old almond trees in Paine, Region 6 of Chile. The experimental design used a randomized block pattern with 10 replications of each experimental condition. Each experimental unit was a shoot of a non Pareil almond tree which was pollinated by bees in Solano and Carmel cultivars. Sufficient bee colonies were used for pollination of the orchard, including trees not receiving an experimental treatment.

Flowers at full bloom were tallied and two weeks later the test branches were sprayed with either a control containing just water, a solution containing HBR at a rate of 1 ppm, a 10 ppm solution of HBR, or a solution of 10 ppm HBR and 10 ppm CPPU.

Final fruit set on each test branch was taken at harvest. The percentage of fruit set was calculated by dividing the number of fruit per branch by the number of flowers counted before treatment and multiplying the result by 100. Results are shown in Table 2 (FIG. 9).

All PGR treatments increased fruit set, with the application of 1 ppm HBR two weeks after full bloom having the greatest effect, increasing fruit set by 21.1 percent over control. The group that was sprayed with the 10 ppm HBR and 10 ppm CPPU solution had kernels which were 11.8 percent larger than the control group.

EXPERIMENT 3.

Branches of Carmel cultivars were selected from a mature almond orchard further comprising Solando and Non Pareil cultivars.

Figure 2:
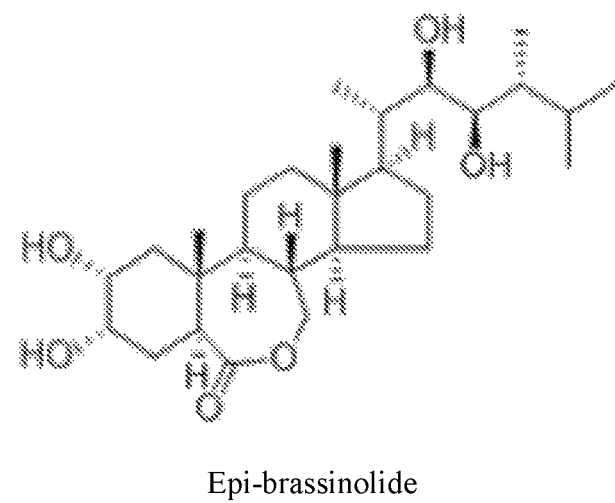
FIG. 2 is the chemical structure of epi-brassinolide.
Figure 4:
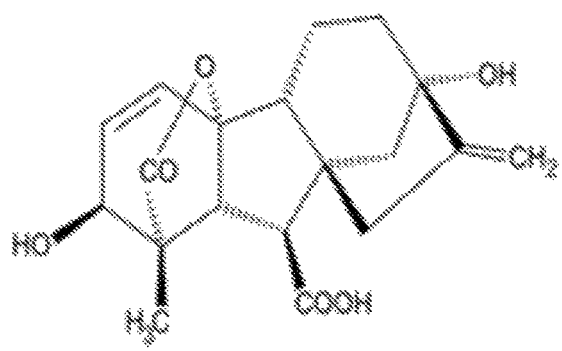
FIG. 4 is the chemical structure of gibberellic acid.

During flowering, the selected branches received either a brassinosteroid treatment (BL, EBL, or HBR) (FIGS. 1, 2, and 3) or a gibberellic acid (FIG. 4) treatment. Four hours after treatment the percent of flowers which contained germinated pollen was determined. Twenty-four hours after treatment the length of each pollen tube was measured. Finally, fruit set was tabulated 50 days after fertilization. Results across the brassinosteroids were similar. The results of the pooled BR treatments and of the GA3 treatments are summarized in Table 3 (FIG. 10). Treatment with the studied PGRs increased pollen germination after four hours (the most effective treatment being 5 ppm HBR), and BR treatment increased pollen tube growth after 24 hours as compared to control. Fruit set at 50 days after flowering was greater in the BR group than either GA3 or control.

Method of Use.

To practice the subject matter of this application a user must first decide if increased almond fruit set is desired. If it is, the user selects at least one plant growth regulator from the group consisting of 28-Homobrassinolide (HBR), Brassinolide (BL), 24-epibrassinolide (epi-BL), Castasterone (CS), 28-Homocastasterone (HCS), Forchlorfenuron (CPPU), and Gibberellic acid (GA3) and prepares a solution having a plant growth regulator concentration as described in the specification and claims. The user would then apply the plant growth regulator solution to the flowers of the tree using methods known in the art when a majority of the flowers of the tree are in the full bloom stage. In any group of trees there will be some variation in flower stage so the user must select an application time when a majority of the flowers are in the full bloom stage. Application of a plant growth regulator in effective from the beginning of the full bloom stage through the beginning of the petal fall stage. Therefore, the effective application period extends from the beginning of full bloom through the point of the petal fall stage, since at any point between the beginning of full bloom and petal fall at least some portion of the flowers will be responsive to treatment with a plant growth regulator. For a treatment to be maximally effective on an orchard, the user must select a time where the largest portion of flowers will be responsive. The fruit of the tree is left to develop and is harvested at an appropriate time.

We claim:

1. A method for increasing the number of edible seeds produced by an Almond tree comprising the steps of applying at least one plant growth regulator selected from the group consisting of Castasterone (CS), 28-Homocastasterone (HCS), and Forchlorfenuron (CPPU) to flowers of said almond tree at a determined time during flowering; allowing the edible seeds to develop to maturity, and collecting the edible seeds from the tree.

2. The method of claim 1 in which the plant growth regulator solution further comprises at least one member of the group consisting of 28-Homobrassinolide (HBR), Brassinolide (BL), 24-epibrassinolide (epi-BL), and Gibberellic acid (GA3).

3. The method of claim 1 in which the determined time during flowering is approximately during the full bloom stage.

4. The method of claim 1 in which the determined time during flowering is approximately two weeks after full bloom.

5. The method of claim 1 in which the determined time during flowering is during the petal fall stage.

6. The method of claim 1 in which the plant growth regulator solution is comprised of 28-homobrassinolide at a concentration of about 1 to 10 parts per million concentration.

7. A method for increasing the number of edible seeds produced by an Almond tree comprising the steps of applying a brassinosteroid and forchlorfenuron to flowers of said almond tree at a determined time during flowering; allowing the edible seeds to develop to maturity, and collecting the edible seeds from the tree.

8. A method for increasing the number of edible seeds produced by an Almond tree comprising the steps of applying a brassinosteroid and forchlorfenuron, said forchlorfenuron present in a concentration between 1 part per million and 10 parts per million, to flowers of said almond tree at a determined time during flowering; allowing the edible seeds to develop to maturity, and collecting the edible seeds from the tree.

* * * * *